United States Patent [19]
Dubief et al.

[11] Patent Number: 5,660,818
[45] Date of Patent: Aug. 26, 1997

[54] BIOFLAVONOIDS AS AGENTS FOR PROTECTING THE PHYSICAL AND/OR COSMETIC PROPERTIES OF KERATINOUS SUPERFICIAL BODY GROWTHS

[75] Inventors: Claude Dubief, Le Chesnay; Damarys Braida-Valerio; Daniele Cauwet-Martin, both of Paris, all of France

[73] Assignee: L'Oreal, Paris, France

[21] Appl. No.: 435,370

[22] Filed: May 5, 1995

[30] Foreign Application Priority Data

May 5, 1994 [FR] France .................... 94 05540

[51] Int. Cl.$^6$ ................. A61K 7/06; A61K 7/40
[52] U.S. Cl. ............... 424/70.1; 424/70.51; 424/70.5; 424/59; 514/847
[58] Field of Search ................. 424/401, 195.1, 424/70.1, 70.2, 70.51, 70.7, 59; 514/897

[56] References Cited

FOREIGN PATENT DOCUMENTS

| 0 329 032 | 8/1989 | European Pat. Off. . |
| 0 461 827 | 12/1991 | European Pat. Off. . |
| 2 207 699 | 6/1974 | France . |
| 2 315 991 | 1/1977 | France . |
| 2 416 008 | 8/1979 | France . |
| 2 578 165 | 9/1986 | France . |
| 2 666 226 | 3/1992 | France . |
| 0 500 437 | 8/1992 | France . |
| 2 673 839 | 9/1992 | France . |
| 2 627 085 | 8/1993 | France . |
| 1 910 561 | 9/1970 | Germany . |
| 4-266809 | 2/1991 | Japan . |
| 5-004906 | 6/1991 | Japan . |

OTHER PUBLICATIONS

Zviak, The Science of Hair Care, 1986, pp. 137, 191–193, 197–198.
JP-A-05 017 321, Japanese Patent Abstract, vol. 17, No. 291 (Goro Kawaguchi) 1993.
JP-A-04 013 691, Japanese Patent Abstracts, vol. 16, No. 164 (Hayashibara Biochem Lab. Inc.) 1992.
JP-A-03 005 423, Japanese Patent Abstract, vol. 15, No. 112 (Ichimaru Pharcos Co.) 1991.
JP-A-04275210, Chemical Abstract, vol. 118, No. 87374, (Tsukada) 1991.
JP-A-63 066 110, Japanese Patent Abstract, vol. 12, No. 297 (Momotani Jiyuntenkan) 1988.

*Primary Examiner*—Salle M. Gardner
*Attorney, Agent, or Firm*—Finnegan, Henderson, Farabow, Garrett & Dunner, L.L.P.

[57] ABSTRACT

A method for strengthening of the mechanical and/or cosmetic properties of keratinous superficial body growths such as the hair, the eyelashes and the nails, by applying certain bioflavonoids, in particular citrus bioflavonoids, as treatment agents to the keratinous superficial body growths. Also, stable compositions containing bioflavonoids and a method for protecting the keratin of superficial body growths from damage by environmental agents.

34 Claims, No Drawings

BIOFLAVONOIDS AS AGENTS FOR PROTECTING THE PHYSICAL AND/OR COSMETIC PROPERTIES OF KERATINOUS SUPERFICIAL BODY GROWTHS

The present invention relates to the use of certain bioflavonoids as treatment agents in cosmetic compositions for the purpose of protecting keratinous superficial body growths such as, in particular, the hair, the eyelashes and the nails. Another subject of the invention is a process for protecting the keratin of these superficial body growths, in particular from various degradations which can be caused to it from damage by environmetal-type factors and the like. The invention also relates to stable compositions containing bioflavonoids.

It is well known that keratinous superficial body growths such as the hair, the eyelashes or the nails are sensitized or weakened at various degree by the action of environmetal agents and light, as well as by the repeated action of various more or less aggressive treatments such as permanent wavings, hair straightening, dyeing, bleaching, washing and the like. The hair acquires, in this case, a rough feel, is difficult to disentangle and to style; in addition, the mechanical properties of the keratinous superficial body growths such as the tensile strength, the breaking load and the elasticity, are impaired in the long run.

To combat the degradation of the hair keratin by light, it has already been proposed to use certain substances capable of screening out light radiation, such as 2-hydroxy-4-methoxybenzophenone-5-sulphonic acid or its salts (FR-A-2,627,085) or 4-(2-oxo-3-bornylidenemethyl) benzenesulphonic acid or its salts (EP-A-329,032) or alternatively lactoferrin (FR-A-2,673,839).

Moreover, certain flavonoids are known for their use in the preparation of cosmetic compositions, as agents for protecting the skin and/or its keratinous superficial body growths against singlet oxygen, as described in Patent Application FR-A-2,687,752. However, not only do these flavonoids not correspond to those used within the framework of the present invention, but in addition this document remains silent on the specific effects which might be obtained by applying the said flavonoids to the hair, the eyelashes or the nails.

However, the inventors have now discovered, unexpectedly and surprisingly, that certain specific flavonoids, as defined below, have a strengthening action on the keratin of the superficial body growths and have a protective effect against the degradation of the keratinous superficial body growths by light. In addition, they offer excellent cosmetic properties to the keratinous superficial body growths, in particular by improving the disentanglement and/or styling and/or softness of the hair.

The inventors have noticed that compositions containing bioflavonoids are not stable. Indeed, these compositions change color, becoming yellow or brown. Their efficiency can also decrease.

The inventors have now discovered that with a particular reducing agent, compositions containing bioflavonoids are stable and do not have the above-mentioned drawbacks.

These discoveries form the basis of the present invention.

In one of its first aspects, the subject of the present invention is thus the use, in a cosmetic composition, of at least one citrus bioflavonoid, as treatment agent for protecting or for strengthening the physical properties, in particular the mechanical properties, of keratinous superficial body growths, and/or as treatment agent for improving the cosmetic properties of keratinous superficial body growths.

The improved mechanical properties are more particularly the tensile strength the breaking load, and the elasticity.

The improved cosmetic properties are, in particular, the disentanglement and/or styling and/or softness of the hair.

Superficial body growths should be understood to mean more particularly the hair, the eyelashes, the eyebrows and the nails. The use according to the present invention is particularly intended for the hair.

Citrus bioflavonoids occur in the rind of citrus fruits such as lemon, orange, mandarin or grapefruit. They are also known for their ability to maintain the blood vessels in good condition by reducing the fragility and the permeability of the capillary vessels (The Merck Index; 1989; page 1243).

According to another aspect of the present invention, the bioflavonoids which can be used within the framework of the present invention are chosen from the compounds of formula (I):

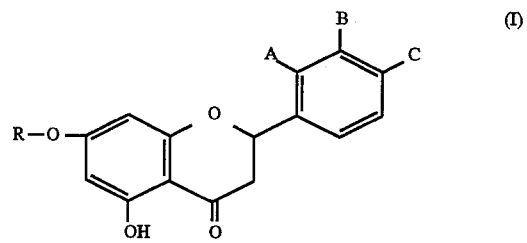

in which

R represents a radical of a sugar

A represents a hydrogen atom or an alkoxy radical having about 1 to 4 carbon atoms, B represents a hydrogen atom or a hydroxyl or alkoxy radical having about 1 to 4 carbon atoms, and C represents a hydrogen atom or a hydroxyl or alkoxy radical having about 1 to 4 carbon atoms. The bioflavonoids which can be used may more preferably be chosen from the compounds of formula (II):

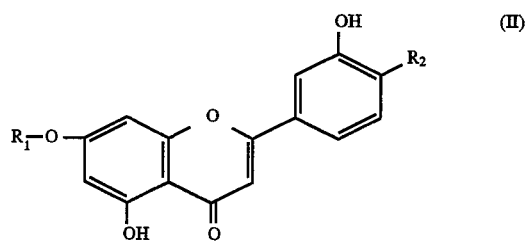

in which $R_1$ designates a 6-O-(6-deoxy-α-L-mannopyranosyl)-β-D-glucopyranosyl radical and $R_2$ designates an alkoxy radical having about 1 to 4 carbon atoms.

The invention also relates, according to another aspect thereof, to the use, in a cosmetic composition, of at least one bioflavonoid as defined in formulae (I) or (II) above, as treatment agent for protecting or for strengthening the physical properties, in particular the mechanical properties, and/or for improving the cosmetic properties, of at least one keratinous superficial body growth.

The improved mechanical properties are more particularly the tensile strength, the breaking load, or the elasticity.

The improved cosmetic properties are, in particular, the disentanglement and/or styling and/or softness of the hair.

The subject of the present invention is also a cosmetic composition containing at least one citrus bioflavonoid and/or at least one bioflavonoid as defined in formulas (I) and (II) above, and at least one reducing agent selected from alkaline and alkaline-earth salts of metabisulphite, erythorbic acid, and cysteine.

Within the framework of the present invention, A preferably represents a hydrogen atom or a methoxy radical, B and C represent, preferably and independently of each other, a hydrogen atom or a hydroxyl or methoxy radical, $R_2$ preferably represents a methoxy radical. R preferably represents a residue chosen from the 6-O-(6-deoxy-α-L-mannopyranosyl)-β-D-glucopyranosyl, 2-O-(6-deoxy-α-L-mannopyranosyl)-β-D-glucopyranosyl and 6-deoxy-α-L-mannopyranosyl groups.

The compounds of formula (I) which are even more particularly preferred are chosen from naringin, neohesperidin, hesperidin and eriodictin.

The compounds of formula (I) and (II) are bioflavonoids which are extracted from plants and can also be obtained according to processes described in "The Flavonoids", Harbone J. B., Mabry T. J., Helga Mabry, 1975, the disclosure of which is hereby incorporated by reference. The bioflavonoids used according to the invention possess a good affinity in relation to keratinous superficial body growths. They strengthen the physical properties of keratinous superficial body growths, especially against degradation by light. They preserve the mechanical properties of keratinous superficial body growths, and especially their tensile strength, their elasticity, their swelling rate in an aqueous medium. The hair thus treated has good cosmetic properties especially with respect to the ease with which they can be disentangled. Nails thus treated split less.

The compounds of formula (I) and (II) occur in extracts of citrus fruits, and in particular of lemon. Such extracts are especially marketed by the company INTERCHEMICAL under the names "CITRUS BIOFLAVONOID COMPLEX 45%", "LEMON BIOFLAVONOID COMPLEX 50%", "GRAPEFRUIT BIOFLAVONOID COMPLEX 25%" and "ORANGE BIOFLAVONOID COMPLEX 25%".

In the compositions for use according to the invention, the compounds of formula (I) and (II) and/or the citrus bioflavonoids generally occur at a concentration of from 0.001 to 10% by weight, and preferably of from 0.005 to 5% by weight relative to the total weight of the composition.

The reducing agent is preferably selected from metabisulphite salts and erythorbic acid. The salts of metabisulphites are preferably sodium or potassium salts. In the compositions according to the invention, the reducing agent generally occurs at a concentration ranging form 0.001 to 3% by weight and preferably from 0.05 to 1% by weight relative to the total weight of the composition.

The compositions can be provided in the form of a monophase or multiphase aqueous or aqueous-alcoholic lotion, of a monophase or multiphase gel, of an emulsion, cream, vesicular dispersion, foam or spray.

The compositions used according to the invention are for example rinse-off or leave-in hair compositions, compositions for treating and/or making up the eyelashes or the eyebrows, such as mascaras, compositions for treating the nails, or nail varnishes.

The hair compositions can be provided in the form of a shampoo, a rinse-off or leave-in conditioner, a styling foam, compositions for permanent waving, hair straightening, dyeing or bleaching, or alternatively in the form of rinse-off compositions, to be applied before or after dyeing, permanent waving or hair straightening or alternatively between the two stages of a permanent waving or a hair straightening.

The compositions can moreover contain conventional cosmetic additives chosen from fatty substances, organic solvents, silicons, thickeners, emollients, surfactants, anionic, cationic, non-ionic or amphoteric polymers, antifoaming agents, conditioning agents such as proteins, vitamins, treatment agents (agents for stopping hair loss, anti-dandruff agents), ceramides such as those mentioned in EP-A-500,437, the disclosure of which is hereby incorporated by reference, colorants, pearling agents, sunscreening agents and especially sulphonic screening agents, perfumes, preservatives, antimicrobial agents, electrolytes, stabilizing agents such as erythorbic acid and sodium metabisulphite, sequestering agents, propelling agents.

More specifically, as fatty substances, there may be used an oil or a wax or a mixture thereof, fatty acids, fatty alcohols, fatty acid esters such as triglycerides of a $C_6$ to $C_{18}$ fatty acid, petroleum jelly, paraffin, lanolin, hydrogenated or acetylated lanolin.

Among the oils, there may be mentioned mineral oils, animal oils, vegetable oils or synthetic oils, and especially liquid paraffin, paraffin oil, castor oil, jojoba oil, sesame oil, as well as silicone oils and gums, isoparaffins and fluorinated or perfluorinated oils.

Among the waxes, there may be mentioned animal, vegetable, mineral or synthetic waxes, and especially beeswax, candelilla wax, ozokerites, microcrystalline waxes as well as silicone waxes and resins.

Among the organic solvents normally used in the cosmetic compositions, there may be mentioned more specifically $C_1$ to $C_6$ lower monoalcohols or polyalcohols such as ethanol, isopropanol, ethylene glycol, diethylene glycol, propylene glycol, glycerol.

The thickening agents can be chosen especially from sodium alginate, gum arabic, cellulose derivatives such as methyl cellulose, hydroxymethyl cellulose, hydroxyethyl cellulose, hydroxypropyl cellulose, hydroxypropyl methyl cellulose, guar gum or its derivatives, xanthan gum, scleroglucans, cross-linked polyacrylic acids.

As surfactants and as polymers, there may be used all those well known in the state of the art, especially for their use in cosmetic compositions.

Of course, persons skilled in the art will be careful to choose the optional additives so that the properties of the composition are not, or are not substantially, impaired by these additives.

The compositions can be provided in the form of a vesicular dispersion of ionic or non-ionic amphiphilic lipids. They are, in this case, prepared especially by swelling the lipids in an aqueous solution so as to form spherules dispersed in the aqueous medium as described in STANDISH & WATKINS, J. Mol. Biol., 13,238 (1965) or in Patents FR-A-2,315,991 and FR-A-2,416,008, the disclosures of all of which are incorporated by reference. The various types of preparation processes are described in "Les liposomes en biologie cellulaire et pharmacologie" [Liposomes in cell biology and pharmacology], Edition INSERM/John Libery Eurotext, 1987, pages 6 to 18, the disclosure of which is hereby incorporated by reference.

The pH of the compositions according to the invention is generally from 3 to 9, preferably from 3 to 6, and most preferably from 3 to 5.

The compounds of formula (I) and (II) can be added to the composition just before use; they are therefore, in this case, packaged separately from the other ingredients of the composition.

The subject of the invention is also a process for protecting the keratin of the keratinous superficial body growths, in particular from damage by environmental agents, and especially light, consisting in applying to the keratinous superficial body growths to be protected, e.g., hair, an effective quantity of at least one compound of formula (I) and/or (II) and/or of a citrus bioflavonoid as defined above, in a cosmetically acceptable carrier, this application being optionally followed by a rinsing with water.

Several examples in accordance with the invention will now be given byway of illustration and with no limitation being implied.

EXAMPLE 1

A conditioner of the following composition was prepared:

| | |
|---|---|
| cetylstearyl alcohol | 2.8 g |
| glycerol mono- and distearate | 0.5 g |
| lanolin | 0.5 g |
| cetyltrimethylammonium chloride in 25% aqueous solution sold under the name "ARQUAD 16–25" by the company AKZO | 0.55 g (AI) |
| mixture of bioflavonoids[(1)] sold under the name "grapefruit Bioflavonoid complex 25%" by the company INTERCHEMICAL | 0.5 g |
| preservatives | qs |
| perfumes | qs |
| water gs | 100 g |

Spontaneous pH: 4.6
[(1)]: The extract contained 21.5% by weight of naringin, 0.7% of hesperidin and 0.7% of neohesperidin.

This conditioner was applied to wet hair after a single shampoo. After rinsing with water, then drying, the hair was smooth, easy to disentangle and was very soft.

EXAMPLE 2

A leave-in treatment hair composition having the following composition was prepared:

| | |
|---|---|
| copolymer of acrylamide and of the sulphonic salt of acrylamido-2-methylpropanesulphonic in reversed emulsion at 40% in an isoparaffin/water mixture sold under the name "SEPIGEL 305" by the company SEPPIC | 1.2 g (AI) |
| mixture of α,ω-dihydroxylated polydimethylsiloxane, of cyclotetradimethylsiloxane and of cyclopentadimethylsiloxane sold under the name "$Q_2$ 1401" by the company DOW CORNING | 20 g |
| mixture of bioflavonoids[(2)] sold under the name "citrus Bioflavonoid complex 45%" by the company INTERCHEMICAL | 0.1 g |
| preservatives | qs |
| perfumes | qs |
| water qs | 100 g |

Spontaneous pH: 6.3
[(2)]: The extract contained 23.95% by weight of naringin, 11.45% of neohesperidin, 1.24% of diosmin and 0.40% of hesperidin.

This treatment composition was applied to washed hair, without rinsing. After drying, the hair was easy to disentangle and had a very good style.

EXAMPLE 3

A shampoo having the following composition was prepared:

| | |
|---|---|
| oxyethylenated sodium and magnesium lauryl ether sulphate (80/20) containing 2.2 moles of ethylene oxide in aqueous solution at 26% by weight, sold under the name "EMPICOL BSD" by the company ALBRIGHT & WILSON | 10 g (AI) |
| cocoylamidopropylbetaine/glycerol monolaurate mixture (25/5) sold under the name "TEGOBETAINE HS" by the company GOLDSCHMIDT at 30% active ingredient | 5 g AI |
| mixture of bioflavonoids sold under the name "citrus Bioflavonoid complex 45%" by the company INTERCHEMICAL | 0.5 g |
| erythorbic acid | 0.5 g |
| perfumes | qs |
| preservatives | qs |
| water qs | 100 g |

This shampoo was applied to wet hair: it had good foaming properties and made it possible to effectively protect the hair from the action of light.

EXAMPLE 4

A mascara, in accordance with the invention, having the following composition was prepared:

| | |
|---|---|
| Phase A: | |
| Beeswax | 6.9 g |
| Carnauba wax | 4.16 g |
| Paraffin | 11.4 g |
| Stearic acid | 7.7 g |
| Phase B: | |
| Black iron oxide | 5.55 g |
| Phase C: | |
| Mixture of bioflavonoids sold under the name "citrus Bioflavonoid complex 45%" by the company INTERCHEMICAL | 0.1 g |
| triethanolamine | 3.8 g |
| Arabic gum | 4.5 g |
| Hydroxyethylcellulose | 0.16 |
| preservatives | qs |
| demineralized water qs | 100 g |

Phase A is melted at 80° C. and Phase B is then introduced and dispersed using a homogenizer for 30 minutes. Phase C is prepared by introducing the first three components of this phase into water maintained at 75° C. An emulsion is then produced by mixing phase C into phase A+B.

The mascara composition is applied to the eyelashes. The eyelashes exhibit good hold.

We claim:

1. A method for protecting or strengthening at least one physical property and/or for improving at least one cosmetic property of at least one keratinous superficial body growth, the method comprising the step of applying to said at least one keratinous superficial body growth for at least one of said purposes of protecting, strengthening, and improving a cosmetically effective amount of a treatment composition comprising at least one citrus bioflavonoid and/or one bioflavonoid selected from the compounds of formula (I):

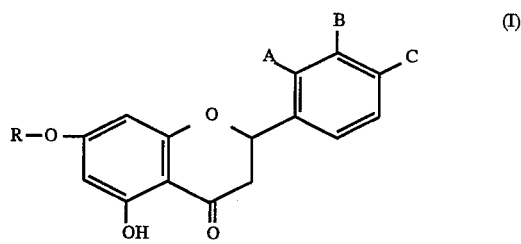

wherein
R represents a radical of a sugar,
A represents a hydrogen atom or an alkoxy radical having from 1 to 4 carbon atoms, B represents a hydrogen atom or a hydroxyl or alkoxy radical having from 1 to 4 carbon atoms, and C represents a hydrogen atom or a hydroxyl or alkoxy radical having from 1 to 4 carbon atoms wherein said composition further comprises at least one reducing agent selected from alkaline-earth metal salts of metabisulfite, erythorbic acid and cysteine.

2. The method according to claim 1, wherein said at least one citrus bioflavonoid and/or one bioflavonoid is selected from the compounds of formula (II):

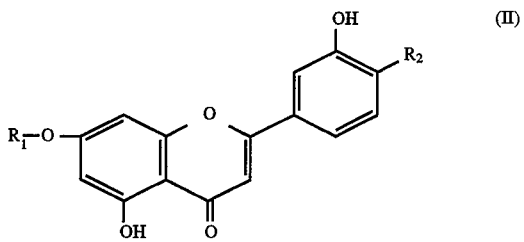

wherein $R_1$ designates a 6-O-(6-deoxy-α-L-mannopyranosyl)-β-D-glucopyranosyl radical and $R_2$ designates an alkoxy radical having from 1 to 4 carbon atoms.

3. The method according to claim 1, wherein A represents a hydrogen atom or a methoxy radical, B represents a hydrogen atom or a hydroxyl or methoxy radical, and C represents a hydrogen atom or a hydroxyl or methoxy radical.

4. The method according to claim 2, wherein $R_2$ represents a methoxy radical.

5. The method according to claim 1, wherein R is a radical selected from the 6-O-(6-deoxy-α-L-mannopyranosyl)-β-D-glucopyranosyl, 2-O-(6-deoxy-α-L-mannopyranosyl)-β-D-glucopyranosyl and 6-deoxy-α-L-mannopyranosyl groups.

6. The method according to claim 1 wherein the compound of formula (I) is selected from naringin, neohesperidin, hesperidin and eriodictin.

7. The method according to claim 1, wherein said at least one citrus bioflavonoid and/or one bioflavonoid is present in a concentration of from 0.001% to 10% by weight relative to the total weight of the composition.

8. The method according to claim 7, wherein said at least one citrus bioflavonoid and/or one bioflavonoid is present in a concentration of from 0.005% to 5% by weight relative to the total weight of the composition.

9. The method according to claim 1, wherein the cosmetic composition is provided in the form of an aqueous or aqueous-alcoholic lotion, a gel, a cream, an emulsion, a vesicular dispersion, a foam or a spray.

10. The method according to claim 1, wherein said improved at least one physical property is a mechanical property.

11. The method according to claim 10, wherein said at least one mechanical property is tensile strength, breaking load, or elasticity.

12. The method according to claim 1, wherein said at least one keratinous superficial body growth is hair.

13. The method according to claim 12, wherein said improved at least one cosmetic property is the disentanglement and/or ease of styling and/or softness of the hair.

14. The method according to claim 1, wherein said cosmetic composition is a rinse-off or leave-in hair composition.

15. The method according to claim 12, wherein said cosmetic hair composition is provided in the form of a shampoo, a rinse-off or leave-in conditioner, a composition for permanent waving, hair straightening, dyeing or bleaching, or alternatively in the form of a rinse-off composition.

16. The method according to claim 15, wherein said cosmetic composition is applied before or after dyeing, permanent waving or hair straightening or alternatively between the two stages of a permanent waving or a hair straightening.

17. The method according to claim 1, wherein said at least one keratinous superficial body growth is eyelashes or eyebrows.

18. The method according to claim 1, wherein said cosmetic composition is a treatment or make-up composition for the eyelashes or the eyebrows.

19. The method according to claim 1, wherein said at least one keratinous superficial body growth is nails.

20. The method according to claim 1, wherein said cosmetic composition is a treatment composition for the nails or a nail varnish.

21. The method according to claim 1, wherein said cosmetic composition contains at least one cosmetic additive.

22. A cosmetic composition containing at least one citrus bioflavonoid and/or at least one bioflavonoid selected from the compounds of formula (I):

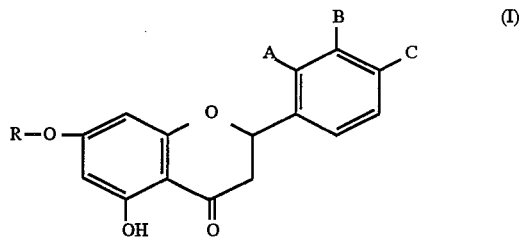

wherein

R represents a radical of a sugar,

A represents a hydrogen atom or an alkoxy radical having from 1 to 4 carbon atoms, B represents a hydrogen atom or a hydroxyl or alkoxy radical having from 1 to 4 carbon atoms, and C represents a hydrogen atom or a hydroxyl or alkoxy radical having from 1 to 4 carbon atoms, wherein said composition further comprises at least one reducing agent selected from alkaline and alkaline-earth salts of metabisulphite, erythorbic acid, and cystsine.

23. The composition according to claim 22, wherein said at least one citrus bioflavonoid and/or one bioflavonoid is selected from the compounds of formula (II):

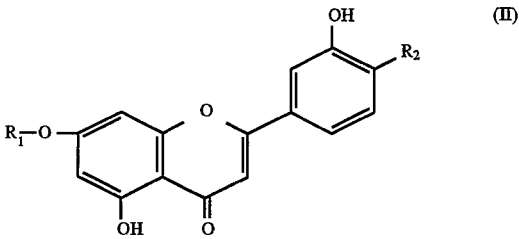

in which $R_1$ designates a 6-O-(6-deoxy-α-L-mannopyranosyl)-β-D-glucopyranosyl radical and $R_2$ designates an alkoxy radical having from 1 to 4 carbon atoms.

24. The composition according to claim 22, wherein said at least one reducing agent is selected from metabisulphite salts and erythorbic acid.

25. The composition according to claim 22, wherein the salts of metabisulphites are sodium or potassium salts.

26. The composition according to claim 22, wherein the pH of said composition is less than 6.

27. The composition according to claim 22, wherein the pH of said composition ranges from 3 to 5.

28. The composition according to claim 22, wherein said at least one reducing agent is present at a concentration of from 0.001 to 3% by weight relative to the total weight of the composition.

29. The composition according to claim 28, wherein said at least one reducing agent is present at a concentration of from 0.05 to 1% by weight relative to the total weight of the composition.

30. The composition according to claim 22, wherein said at least one citrus bioflavonoid and/or at least one bioflavonoid is present at a concentration of from 0.001 to 10% by weight relative to the total weight of the composition.

31. The composition according to claim 30, wherein said at least one citrus bioflavonoid and/or at least one bioflavonoid is present at a concentration of from 0.005 to 5% by weight relative to the total weight of the composition.

32. A method for protecting the keratin of at least one keratinous superficial body growth from damage by environmental agents, comprising the step of applying to said at least one keratinous superficial body growth for the purpose of said protection an effective quantity of a bioflavonoid as defined in claim 1, said bioflavonoid being contained in a cosmetically acceptable carrier wherein said carrier comprises at least one reducing agent selected from alkaline-earth metal salts of metabisulfite, erthorbic acid and cysteine.

33. A method for protecting or strengthening at least one physical property and/or for improving at least one cosmetic property of at least one keratinous superficial body growth, the method comprising the steps of:

(a) applying to said at least one keratinous superficial body growth, for any of the said purposes of protecting, strengthening, and improving, a cosmetically effective amount of a treatment composition comprising at least one citrus bioflavonoid and/or one bioflavonoid selected from the compounds of formula (I):

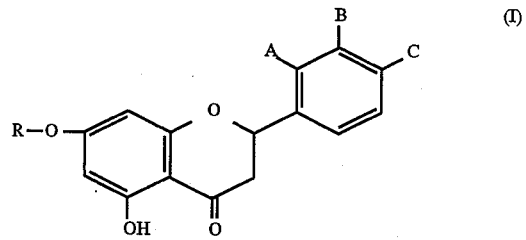

wherein

R represents a radical of a sugar,

A represents a hydrogen atom or an alkoxy radical having from 1 to 4 carbon atoms, B represents a hydrogen atom or a hydroxyl or alkoxy radical having from 1 to 4 carbon atoms, and C represents a hydrogen atom or a hydroxyl or alkoxy radical having from 1 to 4 carbon atoms and at least one reducing agent selected from alkaline-earth metal salts of metabisulfite, erthorbic acid and cysteine; and (b) rinsing said composition out of said at least one keratinous superficial body growth with water.

34. The method of claim 33, wherein said at least one citrus bioflavonoid and/or one bioflavonoid is selected from the compounds of formula (II):

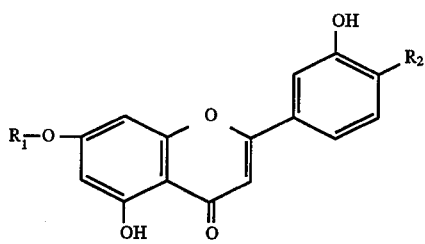

wherein $R_1$ designates a 6-O-(6-deoxy-α-L-mannopyranosyl)-β-D-glucopyranosyl radical and $R_2$ designates an alkoxy radical having from 1 to 4 carbon atoms.

* * * * *